(12) United States Patent
Archibong et al.

(10) Patent No.: US 11,241,466 B2
(45) Date of Patent: Feb. 8, 2022

(54) OKRA AS A SUBSTITUTE FOR CERVICAL MUCUS

(71) Applicant: Meharry Medical College, Nashville, TN (US)

(72) Inventors: Anthony E. Archibong, Antioch, TN (US); G. William Bates, Brentwood, TN (US); Elochukwu J. Ezekakpu, Nashville, TN (US); Lorin W. Simon, Antioch, TN (US); James E. K. Hildreth, Nashville, TN (US)

( * ) Notice: Subject to any disclaimer, the term of this patent is extended or adjusted under 35 U.S.C. 154(b) by 23 days.

(21) Appl. No.: 16/294,839

(22) Filed: Mar. 6, 2019

(65) Prior Publication Data

US 2019/0201464 A1 Jul. 4, 2019

Related U.S. Application Data

(63) Continuation of application No. PCT/US2017/050978, filed on Sep. 11, 2017.

(60) Provisional application No. 62/393,932, filed on Sep. 13, 2016.

(51) Int. Cl.
| | |
|---|---|
| A61K 36/185 | (2006.01) |
| A61P 15/08 | (2006.01) |
| A01N 1/02 | (2006.01) |
| A61B 17/43 | (2006.01) |
| A61F 6/04 | (2006.01) |
| A61K 9/00 | (2006.01) |
| A61K 9/06 | (2006.01) |
| C12N 5/076 | (2010.01) |

(52) U.S. Cl.
CPC ............ *A61K 36/185* (2013.01); *A01N 1/021* (2013.01); *A01N 1/0221* (2013.01); *A61B 17/43* (2013.01); *A61F 6/04* (2013.01); *A61K 9/0034* (2013.01); *A61K 9/06* (2013.01); *A61P 15/08* (2018.01); *C12N 5/061* (2013.01); *A61K 2236/33* (2013.01); *A61K 2236/39* (2013.01); *A61K 2236/53* (2013.01)

(58) Field of Classification Search
None
See application file for complete search history.

(56) References Cited

U.S. PATENT DOCUMENTS 8,202,558 B2   6/2012   Henrickhoff et al.

FOREIGN PATENT DOCUMENTS

| CN | 104983616 A | 10/2015 |
| EP | 1854812 | 1/2009 |
| FR | 2818652 | 6/2002 |
| JP | 08325139 | 12/1996 |
| WO | 2017173030 A1 | 5/2017 |

OTHER PUBLICATIONS

Jain et al. (2012) Pharmacia vol. 1, Issue 3: 84-89. (Year: 2012).*
Roy et al. (2014) Plant Science Today 1(3): 121-130. (Year: 2014).*
Kumar et al. (2013) Int. Res. J. Pharm. App. Sci. 3(4): 129-132. (Year: 2013).*
Lengsfeld, C et al., Glycosylated Compounds from Okra Inhibit Adhesion of Helicobacter pylori to Human Gastric Mucosa, Journal of Agricultral and Food Chemistry, 2004, p. 1495-1503, vol. 52.
Can someone link me to a simple okra gel recipe?, Naturally Curly, available at: https://curltalk.naturallycurly.com/discussion/160458/can-someone-link-me-to-a-simple-okra-gel-recipe.
The International Search Report and The Written Opinion of the International Searching Authority of PCT/US2017/050978, dated Jan. 11, 2018.
Nwoke, K et al., Methanolic extracts of the fruit of *Abelmoschus esculentus* (Okro) causes increase in the serum concentration of some reproductive hormones and decreases total sperm count in male albino wistar rats, European Journal of Pharmaceutical and Medical Research, 205, p. 57-66, vol. 2, No. 5.
Messing, J. et al., Antiadhesive Properties of *Abelmoschus esculentus* (Okra) Immature Fruit Extract against Helicobacter pylori Adhersion, PLoS One, 2014, p. 1-10, vol. 9, No. 1, e84836.
Archibong et al., "*Abelmoschus esculentus* (Okra) Mucilage as a Substitute for Cervical Mucus", Twelfth International Symposium on Recent Advances in Environmental Health Research, Sep. 16, 2015.
Tchounwou, Paul, "Twelfth International Symposium on Recent Advances in Environmental Health Research", International Journal of Environmental Research and Public Health, vol. 13, No. 5, May 4, 2016, pp. 470.
Ameena et al., "Isolation of the mucilages from *Hibiscus rosasinensis* linn, and Okra (*Abelmoschus esculentus* linn.) and studies of the binding effects of the mucilages", Asian Pacific Journal of Tropical Medicine, Hainan Medical College, Singapore, vol. 3, No. 7, Aug. 1, 2010, pp. 539-543.
Shankul Kumar, "Physicochemical, Phytochemical and toxicity studies on gum and mucilage from plant Abelmoschus esculentus", The Journal of Phytopharmacology, Jan. 1, 2014, pp. 200-203.
Tomoda Masashi et al., "Plant Mucilages. XXXVI. Isolation and characterization of a mucilage, "Okra-mucilage R," from the roots of Abelmoschus esculentus", Chemical and Pharmaceutical Bulletin, Pharmaceutical Society of Japan, JP, vol. 33, No. 8, Jan. 1, 1985, pp. 3330-3335.

(Continued)

*Primary Examiner* — Russell G Fiebig
(74) *Attorney, Agent, or Firm* — Bradley Arant Boult Cummings; Timothy L. Capria; Alexandra C. Lynn

(57) ABSTRACT

Artificial cervical fluid is disclosed that contains a mucilaginous extract from the okra plant. The mucilaginous extract can be produced using a hot aqueous extractant or cold extraction process followed by separation of larger particles from the extract. The extract finds many uses, for example as a sperm storage medium, a sperm freezing medium, a sexual lubricant, an artificial insemination medium, and an in vitro fertilization medium.

22 Claims, 7 Drawing Sheets

(56) References Cited

OTHER PUBLICATIONS

Archibong et al., "Fourteenth International Symposium on Recent Advances in Environmental Health Research Oral Presentation Can *Abelmoschus esculentus* (Okra Fruit) Mucilage Protect Human Spermatozoa From Frost Bite?", Sep. 10, 2017.

"Jackson State University | College of Science, Engineering and Technology (CSET) | 14th International Symposium on Recent Advances in Environmental Health Research—College of Science, Engineering and Technology (CSET)", Mar. 10, 2020.

Extended European Search Report of EP 17851373.5, European Patent Office, dated Mar. 18, 2020.

\* cited by examiner

OKRA AS A SUBSTITUTE FOR CERVICAL MUCUS

CROSS-REFERENCE TO RELATED APPLICATIONS

This application is a continuation of and cites the priority of PCT/US17/50978 filed 11 Sep. 2017, which is currently pending, and cites the priority of U.S. 62/393,932 filed 13 Sep. 2016. The contents of PCT/US17/50978 and U.S. 62/393,932 are incorporated herein by reference in their entireties.

STATEMENT REGARDING FEDERALLY SPONSORED RESEARCH OR DEVELOPMENT

This invention was made with government support under grant number U54MD0007593 awarded by the U.S. National Institutes of Health. The government has certain rights in the invention.

In this context "government" refers to the government of the United States of America.

BACKGROUND

Cervical fluid (CF), sometimes referred to as cervical mucus, is produced by glands in the endocervix. Its properties change markedly at various points during the menstrual cycle, allowing it to function either as a barrier against the passage of material (such as spermatozoa and pathogenic organisms) through the cervix or as a selectively permeable barrier that can be penetrated by spermatozoa. Several hundred glands in the endocervix produce 20-60 mg of CF a day, increasing to 600 mg around the time of ovulation. The viscosity of CF varies, due in part to varying mucin concentrations. The viscosity and water content varies during the menstrual cycle; the CF is composed of around 93% water, reaching 98% at mid-cycle. It contains electrolytes such as calcium, sodium, and potassium; organic components such as glucose, amino acids, and soluble proteins; trace elements including zinc, copper, iron, manganese, and selenium; free fatty acids; enzymes such as amylase; and prostaglandins. Its consistency is determined by the influence of the hormones estrogen and progesterone. At mid-cycle around the time of ovulation—a period of high estrogen levels—the CF is thin to allow spermatozoa to enter the uterus, and is more alkaline and hence more hospitable to spermatozoa. It is also higher in electrolytes, which results in the "ferning" pattern that can be observed in drying CF under low magnification; as the CF dries, the salts crystallize, resembling the leaves of a fern. The CF has stretchy character described as "Spinnbarkeit," most prominent around the time of ovulation.

At other stages of the cycle, the CF is thick and more acidic due to the effects of progesterone. This "infertile" CF acts as a barrier to sperm from entering the uterus. Thick CF also prevents pathogens from interfering with a nascent pregnancy. A CF plug, called the operculum, forms inside the cervical canal during pregnancy. This provides a protective seal for the uterus against the entry of pathogens and against leakage of uterine fluids. The operculum is also known to have antibacterial properties. This plug is released as the cervix dilates, either during the first stage of childbirth or shortly before. It is visible as a blood-tinged mucous discharge.

CF has many potential practical uses. CF is used in sperm motility testing. The ability of CF to maintain the viability of sperm indicates that it could be a useful storage or insemination medium. The selective permeability of CF indicates that it could be useful to separate spermatozoa from semen. As natural CF is difficult to collect in large volumes, and as CF with useful properties is only present at certain times during the menstrual cycle, there is a need in the art for an artificial CF with properties like those of "egg white" CF that is present during ovulation.

SUMMARY

It has been unexpectedly discovered that a mucilaginous extract from the fruit of the okra plant (*Abelmoschus esculentus*) can be produced with similar physical and biological properties to human CF, including the ability to be selectively penetrated by motile spermatozoa. This extract finds use for many of the same purposes as natural human CF, as further described below.

In a first aspect, a mucilaginous extract of the fruit of *A. esculentus* is provided, that is the product of the process comprising: (a) extracting a fruit of *A. esculentus* in an aqueous medium, to produce a first extract; and (b) separating a substantially clear mucilaginous fluid from the first extract; wherein the substantially clear mucilaginous fluid has properties similar to those of CF. Examples of such properties include: a Spinnbarkeit of at least about 10 cm when measured according to the test disclosed herein; displays ferning when subjected to the fern test; lacks visible green coloration; and when a semen sample is subjected to a sperm-mucus penetration test using the clear mucilaginous fluid in place of cervical mucus, spermatozoa that penetrate into the clear mucilaginous fluid have a significantly better indication of fertility than do spermatozoa in the semen sample.

In a second aspect, a storage medium for spermatozoa is provided, the medium comprising a mucilaginous extract of the fruit of *Abelmoschus esculentus* and a multiplicity of spermatozoa.

In a third aspect, a method of sperm preservation is provided, comprising a freezing and storage medium comprising a mucilaginous extract of the fruit of *Abelmoschus esculentus* and a multiplicity of spermatozoa.

In a fourth aspect, a coated condom is provided, comprising a condom in contact with a volume of a mucilaginous extract of the fruit of *A. esculentus* sufficient to at least partially coat the condom.

In a fifth aspect, a method of artificial insemination is provided, the method comprising inseminating a subject with a suspension of spermatozoa, the suspension comprising a mucilaginous extract of the fruit of *A. esculentus* and a multiplicity of spermatozoa suspended therein.

In a sixth aspect, a method of in vitro fertilization is provided, comprising: contacting a mixture of the extract of the first aspect and a plurality of spermatozoa with an unfertilized egg in vitro to create a fertilization mixture, incubating the fertilization mixture for a period of time sufficient for fertilization to occur and create an embryo, and transferring the embryo to the uterus of a subject.

In a seventh aspect, a method of providing artificial vaginal lubrication is provided, comprising applying a mucilaginous extract of the fruit of *A. esculentus* vaginally to a subject.

In an eighth aspect, a method of making a mucilaginous extract of the fruit of *A. esculentus* is provided, the method comprising extracting a fruit of *A. esculentus* in an aqueous medium, to produce a first extract; and separating a substantially clear mucilaginous fluid from the first extract.

In a ninth aspect, an apparatus for collecting viable spermatozoa is provided, the apparatus comprising a semen receptacle and a hollow elongate conduit connected to the semen receptacle, wherein the hollow elongate conduit is intended to contain the mucilaginous extract of the first aspect.

In a tenth aspect, a method of in vitro fertilization is provided, comprising: recovering viable spermatozoa from a semen sample into a mucilaginous extract of the fruit of *A. esculentus* with the apparatus described in the ninth aspect, contacting the viable spermatozoa with an unfertilized ovum in vitro to create a fertilization mixture, incubating the fertilization mixture for a period of time sufficient for fertilization to occur and create an embryo, and transferring the embryo to the uterus of a subject.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 1A: placing the pinhole in the bottom of the centrifuge tube. FIGS. 1B-1C: collection of extract. FIG. 1D: measuring the Spinnbarkeit of the mucilaginous extract.

FIG. 5A shows the semen control (no mucilaginous extract). FIG. 5B shows the sample taken from the capillary containing mucilaginous extract.

DETAILED DESCRIPTION

A. Definitions

Figure 1A:
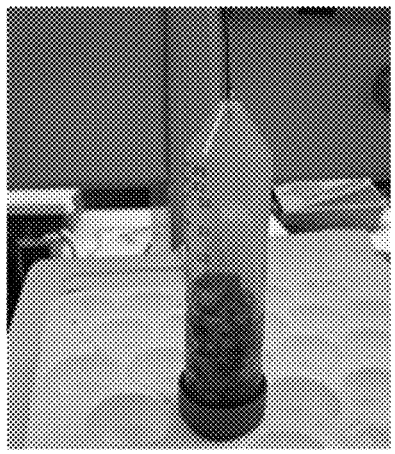
FIGS. 1A-1D: extraction of the okra fruits.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well-known functions or constructions may not be described in detail for brevity or clarity.

The terminology used herein is for the purpose of describing particular embodiments only and is not intended to be limiting. As used herein, the singular forms "a", "an," and "the" are intended to include the plural forms as well, unless the context clearly indicates otherwise.

The terms "first," "second," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20%, preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

Terms such as "administering" or "administration" include acts such as prescribing, dispensing, giving, or taking a substance such that what is prescribed, dispensed, given, or taken actually contacts the patient's body externally or internally (or both). In embodiments of this disclosure, terms such as "administering" or "administration" include self-administering, self-administration, and the like, of a substance. Indeed, it is specifically contemplated that instructions or a prescription by a medical professional to a subject or patient to take or otherwise self-administer a substance is an act of administration.

The terms "prevention," "prevent," "preventing," "suppression," "suppress," and "suppressing" as used herein refer to a course of action initiated prior to the onset of a clinical manifestation of a disease state or condition so as to reduce the likelihood or severity of such clinical manifestation of the disease state or condition. Such reduction of the likelihood or severity need not be absolute to be useful.

The terms "treatment", "treat," and "treating" as used herein refer to a course of action initiated after the onset of a clinical manifestation of a disease state or condition so as to eliminate or reduce such clinical manifestation of the disease state or condition. Such treating need not be absolute to be useful.

The terms "in need of treatment" and "in need of prevention" as used herein refer to a judgment made by a caregiver that a patient requires or will benefit from treatment or prevention. This judgment is made based on a variety of factors that are in the realm of a caregiver's expertise, but that includes the knowledge that the patient is ill, or will be ill, as the result of a condition that is treatable by a method or composition of the present disclosure.

The term "individual," "subject," or "patient" as used herein refers to any animal, including mammals, such as mice, rats, other rodents, rabbits, dogs, cats, swine, cattle, sheep, horses, or primates, and humans. The term may specify male or female or both, or exclude male or female.

Terms such as "comprise" and "include" as used herein are inclusive, and non-exclusive, and should therefore be construed to mean "comprise/include but are not limited to." Permissive and optional terms such as "may" or "some embodiments" as used herein are also inclusive and non-exclusive.

B. Mucilaginous Extracts and Methods of Making the Same

An artificial CF is provided, made of a mucilaginous extract of the fruit of *A. esculentus* (referred to herein by its common name, okra). Like CF itself, the extract finds many uses related to fertility and sex, including such uses as a sexual lubricant, a sperm storage medium, a medium for assisted fertility procedures, a sperm penetration test medium, and an antibacterial agent.

In a general embodiment of the extract, it is the product of the process comprising: (a) extracting an okra fruit in an aqueous medium, to produce a first extract; and (b) separating a substantially clear mucilaginous fluid from the first extract. In this context "substantially clear" means that macroscopic (visible) particles have been removed from the extract. Some embodiments of the mucilaginous fluid are completely clear, meaning that the particulate fraction has been removed to the extent that the mucilaginous fluid does not appear cloudy to the unaided eye. Such removal may be achieved by any means known in the art. For example, a substantially clear mucilaginous fluid may be produced by straining the first extract through one or more pores of about 1 mm diameter or less. In a specific embodiment, the first extract is drained through a single pore of about 1 mm diameter under the force of gravity, which results in a substantially clear mucilaginous fluid. Other means include filtration, centrifugation, settling (with or without flocculants), and vortex separation.

The rate and efficiency of extraction may be improved by chopping the fruit into two or more pieces. In an exemplary embodiment the fruit is chopped into slices about 1-2 mm thick. Prior to any chopping steps the seeds may be removed, or the ribs may be removed, or both (doing so has been observed to eliminate a greenish color in the extract that is otherwise present—although this color is not known to affect the properties of the extract).

The outer surface of the fruit may be sanitized prior to extraction to reduce the likelihood of microbial contamination of the extract. Such sanitation may be performed using chemical sanitizers, such as an ethanol solution (for example, 70% v/v ethanol in water). Ethanol has the advantage of low toxicity and high partial vapor pressure that results in rapid evaporation. Other chemical sanitizers could also be used. It is contemplated that other microbicidal agents could be used, such as gamma radiation or combined heat and pressure.

The extraction step may be carried out at elevated temperature. For example, the extraction may be performed by boiling the fruit in the aqueous medium. Water (as from a municipal water supply) has been found to be particularly suitable for use when the fruit is boiled. Boiling has the advantage of completing the extraction at a rapid rate. Alternatively, extraction may be performed at a lower temperature. At such lower temperatures extraction may take longer than at a boiling temperature; however, lower temperature extraction has the advantage of producing an extract without the green color. For example, in a specific embodiment extraction is performed at 4° C. for 4 hours. Agitation may be used to increase the rate of extraction as well. Extraction at lower temperature may also be performed with water, and it has also been found that lower temperature extraction may be performed with human tubal fluid (HTF) or HTF medium. HTF medium is a synthetic defined medium that is commercially available (for example, from Irvine Scientific, Santa Ana, Calif. USA). Typically HTF medium is buffered against pH drift using a carbonate-$CO_2$ buffer system, in which case it is referred to in this disclosure as "bicarbonate buffered HTF medium." Other kinds of HTF media are available, for example, HEPES buffered HTF medium is available from Irvine Scientific, Santa Ana, Calif. USA. In further embodiments of the mucilaginous fluid the HTF may comprise albumin, such as human serum albumin, to facilitate extraction. A specific embodiment of the aqueous extractant contains 0.5% w/v human serum albumin or bovine serum albumin.

As stated above, the substantially clear mucilaginous fluid has properties similar to those of CF. Examples of such properties include: a Spinnbarkeit of at least about 10 cm when measured according to the test disclosed herein; displays ferning when subjected to the fern test; lacks visible green coloration; and when a semen sample is subjected to a sperm-mucus penetration test using the clear mucilaginous fluid in place of cervical mucus, sperm that penetrate into the clear mucilaginous fluid have a significantly better indication of fertility than do sperm in the semen sample. Each of these properties, on its own, confers significant utility to the mucilaginous fluid.

Spinnbarkeit is the elastic quality of a fluid, and it is specifically measured as a characteristic of mucus of the uterine cervix, especially shortly before ovulation. As is known in the art, the Spinnbarkeit of CF decreases shortly before ovulation. Functionally, this elastic quality contributes to the lubricating qualities of the mucilaginous fluid. It also presents a mechanical barrier to non-motile semen components, such as prostaglandins, which acts as a selective barrier that admits spermatozoa but excludes other components. This property is advantageous in a medium for assisted reproduction procedures and as a medium for use in a sperm penetration test. Spinnbarkeit is measured by contacting the surface of the fluid with an object, such as a glass pipette or polypropylene centrifuge tube, and raising the object above the level of the fluid. A thread of adhered fluid will form, and the object is progressively raised until the thread breaks. Spinnbarkeit is thus measured as a distance. Some embodiments of the clear mucilaginous fluid have a Spinnbarkeit of at least about 10 cm. In further embodiments the clear mucilaginous fluid has a Spinnbarkeit of at least about 15 cm.

The fern test detects solutes in CF, which crystalize as the fluid evaporates, forming microscopic structures reminiscent of the leaves of a fern on a stem that can be viewed under a low-power microscope. The fern test is often used to provide evidence of the presence of amniotic fluid in CF, and is used in obstetrics to detect rupture of membranes and onset of labor. Ferning is due to the presence of sodium chloride in the CF, which is frequently due to estrogen's effects in vivo. The artificial CF described herein under some conditions displays ferning when observed by the fern test. The ferning that has been observed indicates similar composition to the follicular phase of the menstrual cycle.

Sperm that penetrate into certain embodiments of the clear mucilaginous fluid have a significantly better indication of fertility than do sperm in the semen sample. These qualities can be measured using the cervical mucus penetration test (CMPT—also called the sperm penetration test). The CMPT is a widely used method known by those of ordinary skill in the art.

As referred to in this disclosure, the CMPT is the standard protocol of Tang et al., *Human Reproduction* 14:2812-2817 (1999). All media used in this test must be pre-equilibrated to 37° C. Circular cross-section capillary tubes are recommended for use. Each tube is filled by aspiration using a 1 mL syringe and a plastic tube attached to the upper end of the capillary while the lower end is dipped into a pool of cervical mucus, mucilaginous extract, or other media. A column of medium is aspirated into the tube so that the upper meniscus is close but not at the top of the tube. Great care should be taken to avoid trapping air bubbles within the column. The top of the tube is then sealed with PLASTICINE and any trailing medium should be cut off the lower end to produce a flat interface. Approximately 100 µL of liquefied semen should be placed in the bottom of a small conical plastic tube and a capillary tube containing the cervical mucus or other media placed with its open end in the semen. Two semen reservoirs and capillary tubes will then be mounted on a microscope slide as shown in the WHO manual (World Health Organization (1999) *WHO Laboratory Manual for the Examination of Human Semen and Sperm-Cervical Mucus Interaction*; Cambridge University Press, Cambridge), following which, the slides are placed in a Petri dish containing damp sponges to maintain humidity and prevent drying of the semen and media. It is recommended that capillary tubes be incubated in the horizontal position for 60 minutes. Subsequently, the slides are removed from the Petri dishes and the capillary tube viewed under bright field illumination with a 20× phase contrast objective lens and 10× oculars. The microscope stage should be adjusted to select a focal plane incorporating the central axis of the capillary and, at this magnification, the microscope field width approximates the inner diameter of the capillary tube. The length of the tube is then scanned to establish the distance furthest from the semen reservoir attained by spermatozoa.

In addition, the mucilaginous fluid may have one or more properties that are found not necessarily present in human CF. For example, okra extracts have been observed to have anti-adhesive properties against certain microbes, specifically *Helicobacter pylori*. Consequently it is contemplated that the mucilaginous fluid may have anti-adhesive properties against viruses and microorganisms.

The mucilaginous fluid provided herein serves as an effective substitute for CF in the CMPT, as it is selectively penetrated by sperm with high viability. When a semen sample is subjected to a sperm-mucus penetration test using some embodiments of the clear mucilaginous fluid in place of cervical mucus, sperm that penetrate into the clear mucilaginous fluid have a significantly higher rate of normal morphology as compared to spermatozoa in the semen sample. When a semen sample is subjected to a sperm-mucus penetration test using further embodiments of the clear mucilaginous fluid in place of cervical mucus, sperm that penetrate into the clear mucilaginous fluid have a significantly higher rate of progressive motility as compared to spermatozoa in the semen sample. When a semen sample is subjected to a sperm-mucus penetration test using still further embodiments of the clear mucilaginous fluid in place of cervical mucus, sperm that penetrate into the clear mucilaginous fluid have a significantly higher grade of motility as compared to spermatozoa in the semen sample. In this context, the property is "significantly higher" if a person skilled in the art, such as a board-certified andrologist, would note that the property is markedly higher when using standard clinical tests.

Without wishing to be bound by any hypothetical model, it is believed that the mucilaginous extract contains four main polysaccharides and protein. The polysaccharides are dominated by rhamnose, galactose, and uronic acid monomers. Some embodiments of the extract comprise 7-28% mol/mol rhamnose, 12-50% mol/mol galactose, 14-56% mol/mol uronic acids, and 12-48% mol/mol protein (in which mole percent refers to the molarity of the specific fraction divided by the combined molarity of all sugar monomers, uronic acids, and proteins after hydrolysis of the polysaccharides). Further embodiments of the extract comprise one or more of 11.0-16.6% mol/mol rhamnose, 19.8-29.6% mol/mol galactose, 22.8-34.2% mol/mol uronic acids, and 19.0-28.4% mol/mol protein. Still further embodiments comprise one or more of 13.8% mol/mol rhamnose, 24.7% mol/mol galactose, 28.5% mol/mol uronic acids, and 23.7% mol/mol protein. Further embodiments of the extract further comprise one or more of 0.75-1.5% mol/mol arabinose, 0.4-1.2% mol/mol xylose, 0.45-1.8% mol/mol mannose, and 3.0-12% glucose. Still further embodiments of the extract may comprise one or more polysaccharides having any one of the structures shown in FIGS. 6A-D.

C. Cryopreservation Medium for Spermatozoa

The artificial CF described above finds use as cryopreservation medium for sperm. The cryopreservation medium comprises any embodiment of the artificial CF described above, and may further comprise a plurality of spermatozoa. The medium may also include any of several useful cryopreservative components, including one or more components such as glycerol, citrate, egg yolk, and antibacterial agents. Glycerol may be present at any concentration known in the art to preserve cellular viability upon freezing; examples of such concentrations include about 5-25% v/v, more specifically about 10-20% v/v, 12% v/v, and 15% v/v. Citrate and egg yolk can be used to reduce osmotic stress on the cells during penetration by glycerol. Antibiotics can be used to reduce the likelihood of microbial contamination of the sample. Such components may be used at concentrations that would be used in standard glycerol and glycerol-egg yolk cryopreservatives, in which the balance of the composition is the artificial CF.

The cryopreservative can be used in a method of sperm preservation. The method involves providing a composition comprising the cryopreservative in combination with a plurality of spermatozoa, and freezing the composition. In some embodiments of the method the composition is frozen at a temperature of about −10° C. or below; in further embodiments the composition is frozen at −40° C. or below; in still further embodiments the temperature is about −80°, −100°, −140°, −160°, −180°, or −190° C. or below. Any embodi-

D. Methods of Use

Various methods of using the extract and the cryopreservation medium are provided.

One such method is a method of assisted fertility using any embodiment of the extract or storage medium described above combined with a plurality of spermatozoa. A first general embodiment of the method of assisted fertility is an in vitro fertilization method, comprising contacting a mixture of any embodiment of the extract or storage medium described above and a plurality of spermatozoa with an unfertilized egg in vitro to create a fertilization mixture, incubating the fertilization mixture for a period of time sufficient for fertilization to occur and create an embryo, and transferring the embryo to the uterus of a subject. Any variants of in vitro fertilization that are known in the art may be used. A second general embodiment is a method of artificial insemination comprising providing a mixture of a plurality of spermatozoa with any embodiment of the extract or storage medium described above, and placing the mixture into the uterus of a subject. Any variants of artificial insemination that are known in the art may be used.

Another general embodiment of a method of assisted fertility comprises recovering viable spermatozoa from semen into the mucilaginous extract of the fruit of *A. esculentus* with the apparatus described below, contacting the spermatozoa to an unfertilized egg in vitro to create a fertilization mixture, incubating the fertilization mixture for a period of time sufficient for fertilization to occur and create an embryo, and transferring the embryo to the uterus of a subject. The method may also comprise separating the extract from the spermatozoa, for example by centrifugal washing.

Another such method is a method of providing vaginal lubrication comprising applying any embodiment of the extract described above to a subject. Additional components may include additional lubricants (such as glycerin and cellulose ether), gelling agents, moisturizers (such as carrageenan), flavorings, fragrances, microbicides, spermicides, and antivirals. Some embodiments of the method may be intended to provide lubrication that does not impair fertility, in which case the spermicide would be specifically omitted. The extract is applied to the genitalia of the subject, whether directly or on an intervening structure such as a condom. For example, the extract may be applied vaginally or phallically.

E. Sperm Penetration Test and Kit

A test is provided for measuring the motility of spermatozoa by measuring their ability to penetrate okra mucilage. The test comprises contacting a semen sample to a volume of mucilaginous okra extract, incubating the sample at about physiological temperature for a period of time, and measuring the distance of a leading spermatozoon from a location at which the semen sample was introduced. The test may be conducted on a glass surface, such as the surface formed by the interface of a glass slide and a coverslip. A path or "track" may be formed to corral the spermatozoa, enhancing the ease of measuring the distance traveled by the phalanxes. Incubation conditions may be any that are typically used during sperm motility tests; in a specific embodiment incubation is conducted at 37° C. under a 5% v/v mixture of air and $CO_2$. The semen sample can be classified as of normal motility or subnormal motility based on a benchmark distance. The benchmark distance may be established by the use of a control sample at the time of the test, or a previously established standard benchmark may be used. The classification of the semen sample may be made pursuant to a statistical test that incorporates a measure of central tendency and a measure of variation; such tests include Student's t-test, an ANOVA, and a confidence limit.

F. Coated Condom

A coated condom is provided comprising a condom in contact with a volume of any embodiment of the extract described above, the volume being sufficient to at least partially coat the condom. Some embodiments of the condom are entirely coated by the extract. A further embodiment of the condom is at least coated with the extract on its exterior surface. The condom may be constructed of any material known as suitable in the art, for example, latex, polyurethane, polyisoprene, lamb intestine, and nitrile rubber.

In some embodiments of the condom, the condom is coated by any embodiment of the vaginal lubricant described above.

G. Apparatus for Collecting Viable Spermatozoa

An apparatus for collecting viable spermatozoa is provided, the apparatus comprising a semen receptacle and a hollow elongate conduit connected to, or in fluid communication with, the semen receptacle, wherein the hollow elongate conduit is intended to contain any embodiment of the extract described above. A sample containing a plurality of spermatozoa is placed in the semen receptacle, and allowed to remain in contact with the extract for a period sufficient to allow motile spermatozoa to penetrate the extract. As explained in more detail in the example below, the extract has been observed to be selectively permeable to morphologically normal and motile spermatozoa.

Some embodiments of the apparatus comprise a valve positioned to reversibly close an end of the hollow elongate conduit against the passage of spermatozoa. Some embodiments of the valve prevent the passage of any particles, creating a watertight seal when closed. Further embodiments of the valve are configured to prevent the passage of particles above a certain effective diameter. A collection vessel may be positioned to receive material from the valve (when open).

H. Example 1: Method of Making Mucilaginous Extract

Figure 1B:
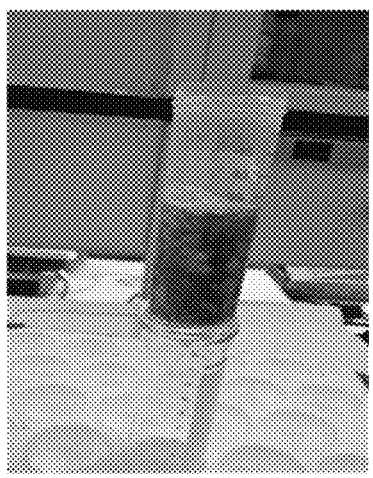
Figure 1C:
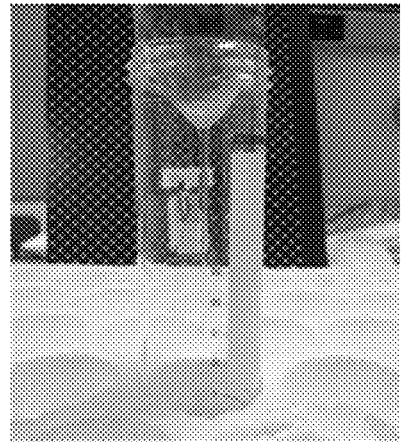

An 8"×8" aluminum foil sheet was sterilized with 70% ethanol and wiped dry with a task wipe, such as KIM-WIPES. Six okra fruits were thoroughly washed with a mild soap solution prior to being thoroughly rinsed with tap water (5×500 mL) followed by DI water (1×500 mL), and sterile wiped with a task wipe pre-soaked in 70% ethanol. After allowing ethanol film on okra fruits to dry (15-20 min), the fruits were placed on the sterile aluminum foil and okra slices (1-2 mm) were prepared with a sterile scalpel blade. Ten grams of sliced okra fruit portions were placed in each of three 50 mL centrifuge tubes containing 15, 20, or 25 mL of HTF-bicarbonate solution (25 mM of $Na_2CO_3$ in buffered human tubal fluid [HTF] containing 0.5% human serum albumin). Extraction tubes were rocked at 4° C. on a tissue rocker/shaker for 4 hours. Each extraction centrifuge tube was inverted and the bottom sterilized with a 70% ethanol wipe. Using a pre-heated 18 G needle, a pinhole was created at the center of the bottom of the tube with a pore size of approximately 1.0 mm (large enough to permit fluid escape but small enough to prevent okra seeds escape—FIG. 1A). Each extraction tube was inverted (cap side up) over another uncapped 50 mL centrifuge tube (FIG. 1B). The cap to the extraction tube was loosened to permit the clear extracted okra mucus to drip under gravitational force into the collection tube (FIG. 1C). The extracted mucus was clear and devoid of chlorophyll pigment.

Figure 1D:
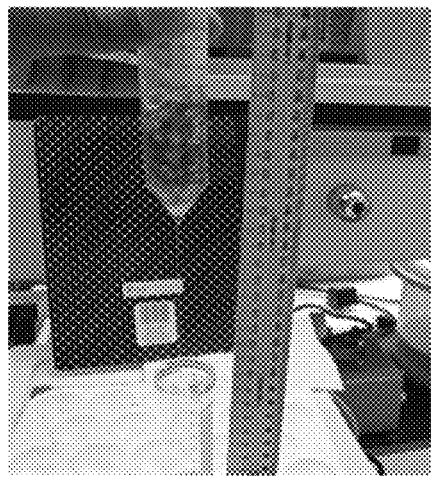
Figure 2A:
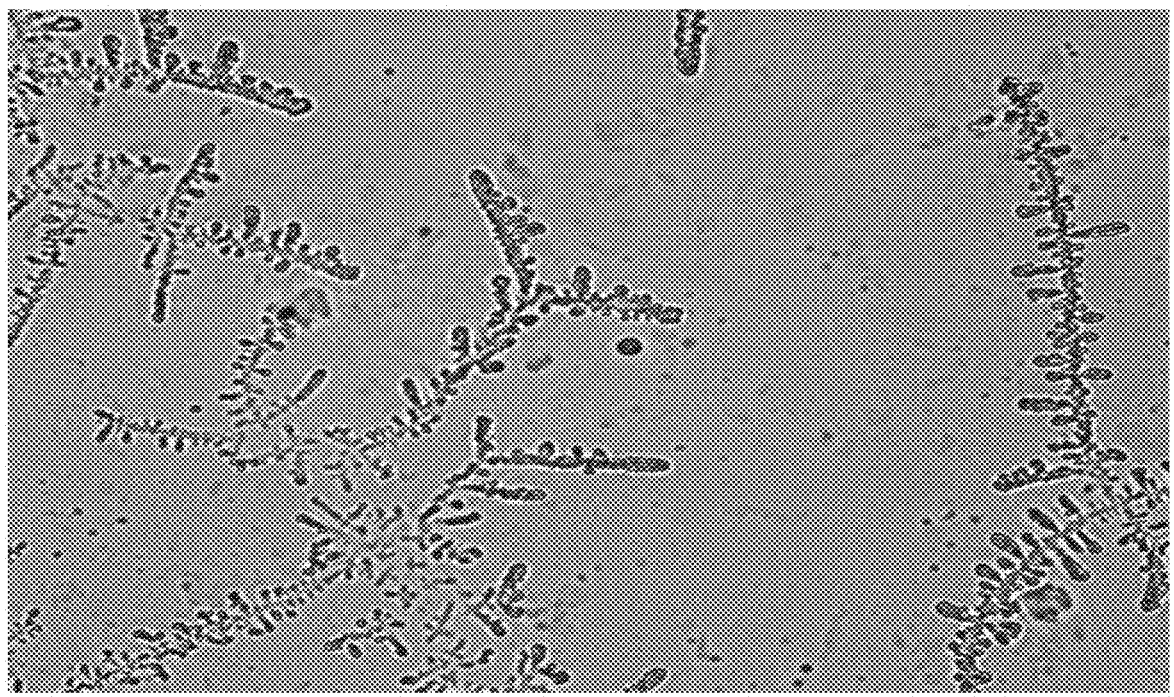
FIGS. 2A-2B: comparison of the ferning patterns of human cervical mucus (FIG. 2A) and the mucilaginous extract (FIG. 2B).
Figure 2B:
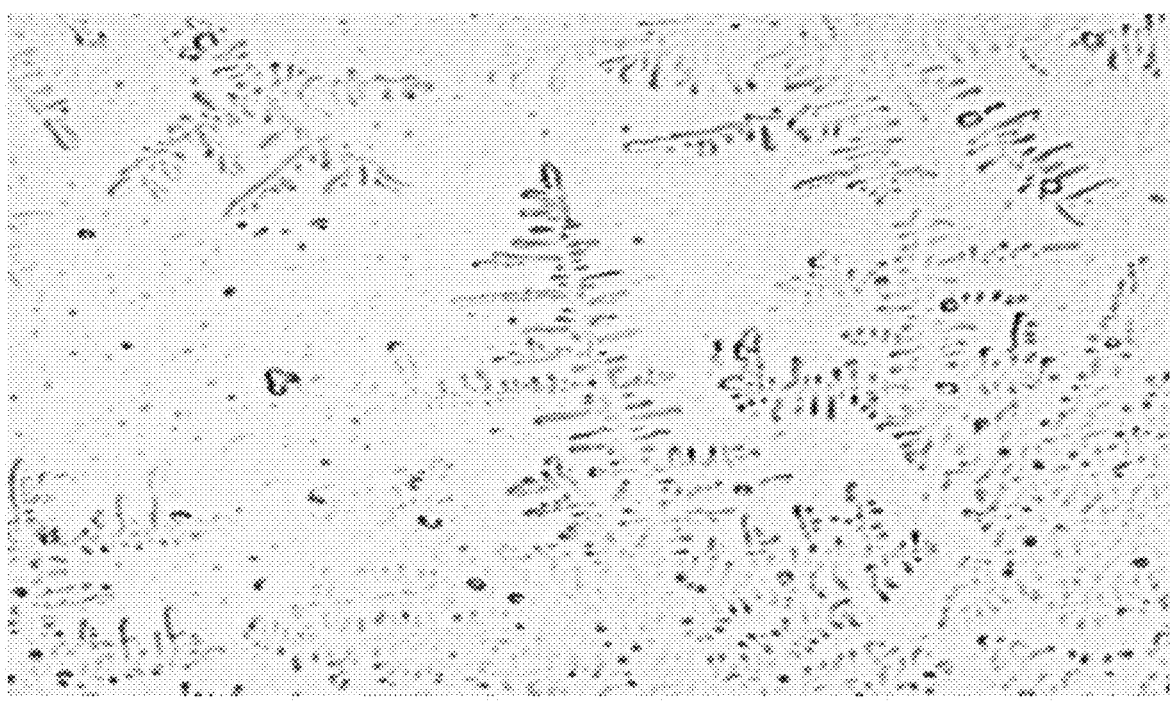

A ruler was placed by the side of the collection tube and the length of each mucus string was measured before breaking, as shown in FIG. 1D. This measurement corresponded to the stretchability or Spinnbarkeit of the mucilaginous extract. The extraction efficiency of the mucus was based on the amount of mucus recovered relative to the amount of HTF-bicarb used to extract the okra mucilage and did not differ significantly among preparations (30-36%). The Spinnbarkeit (stretchability) was similar among preparations (greater than 19 cm). The ferning pattern of mucilaginous extract was similar among preparations and mirrors the pattern observed in the follicular phase of the menstrual cycle (see FIGS. 2A-2B). The mucilaginous extract was stored at −80° C. for 5 weeks and longer.

I. Example 2: Sperm Penetration Test Using Mucilaginous Extract

The sperm penetration test protocol used in this application is a modification of the method of Tang et al. (1999), supra. Unless otherwise specified, all media were pre-equilibrated to 37° C. Non-treated Kimble circular cross-section capillary tubes, 75 mm in length and inner diameter 1.1 mm (Fisher Scientific, PA) were used. Each tube was filled by aspiration using a 1 mL tuberculin syringe and a plastic tube attached to the upper end of the capillary while the lower end was dipped into the *A. esculentus* mucus (100 µL) or equivalent volume of control medium (bicarbonate-buffered HTF containing 5% human serum albumin). An approximately 6.0 cm column of *A. esculentus* mucus or control medium was aspirated into the tube so that the upper meniscus was 1-2 cm from the top of the tube, while being careful not to trap air bubbles within the column. The top of each tube was sealed with modeling clay, such as PLASTI-CINE, and any trailing medium was cut off the lower end to produce a flat interface. Approximately 100 µL of liquefied semen was placed in the bottom of a small conical plastic tube and a capillary tube containing *A. esculentus* mucus or control medium placed with its open end in the semen. This preparation was replicated five times with semen samples from different donors. The two semen reservoirs and capillary tubes were mounted on a microscope slide as demonstrated in the WHO manual (WHO, 1999). The slides were then placed in a Petri dish and incubated in the horizontal position for 60 minutes at 37° C. in an atmosphere of 5% $CO_2$ in humidified air.

After 1 h, the motility of the spermatozoa was determined for the control and the mucilaginous extract sample by viewing the capillary tubes with a phase contrast microscope at 200× magnification. A significant mean number of spermatozoa (>25±3 spermatozoa under 200× magnification) penetrated the mucilaginous extract and traveled approximately 45 mm (migration distance) within 1 h of initiation of interaction with semen versus 10±4 spermatozoa in the control preparation.

Figure 5A:
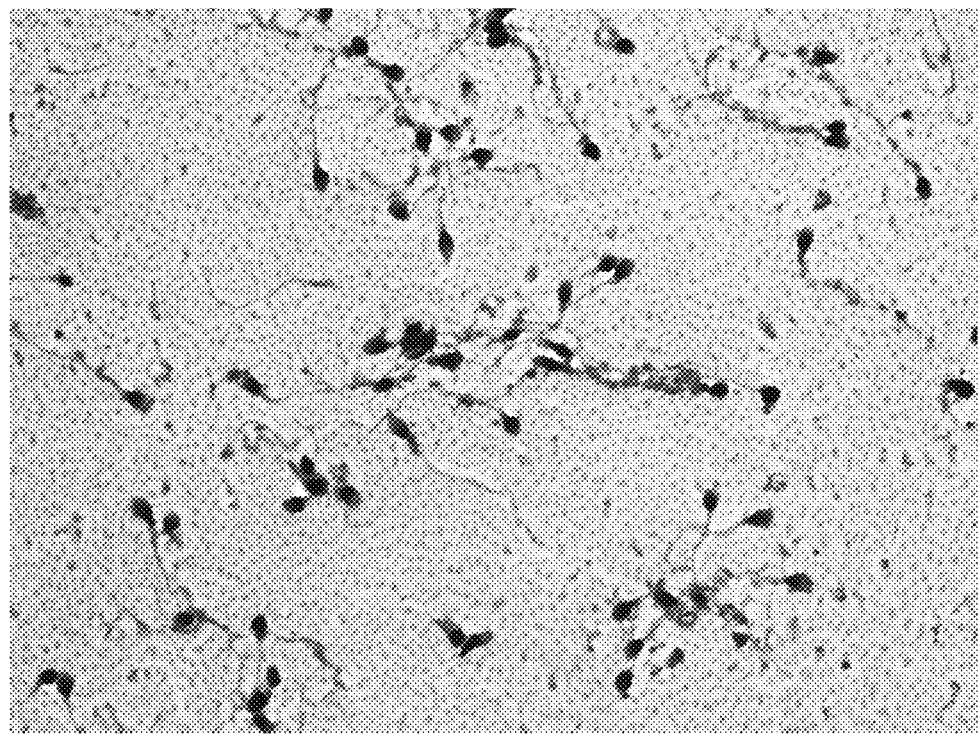
FIGS. 5A-5B: lack of penetration of mucilaginous extract by spermatozoa from semen of an infertility patient.
Figure 5B:
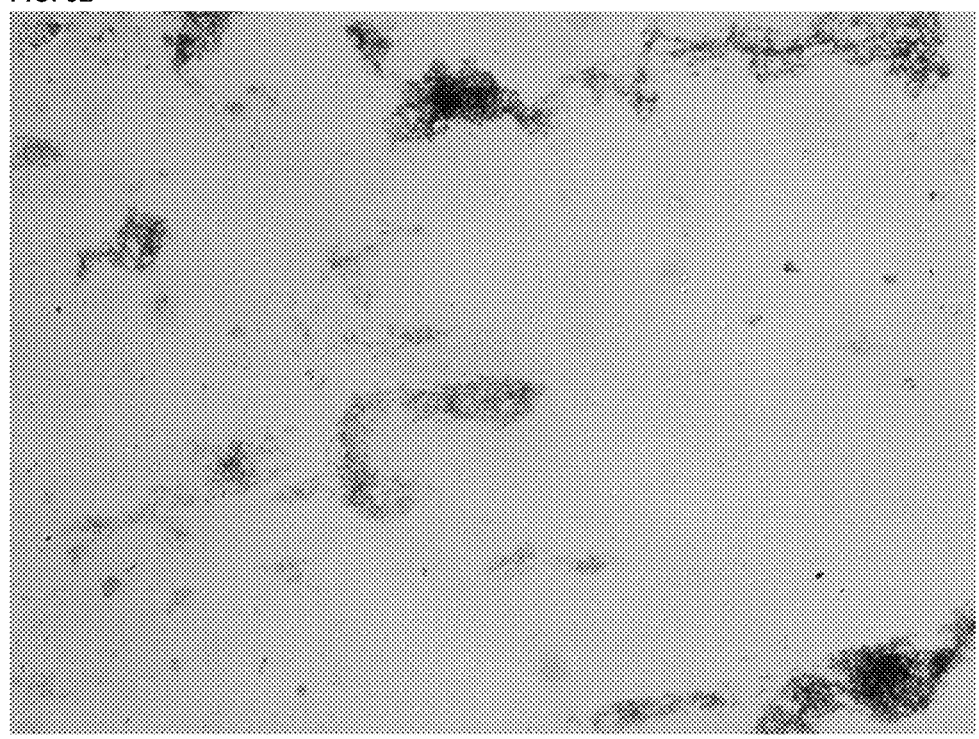
Figure 6A:
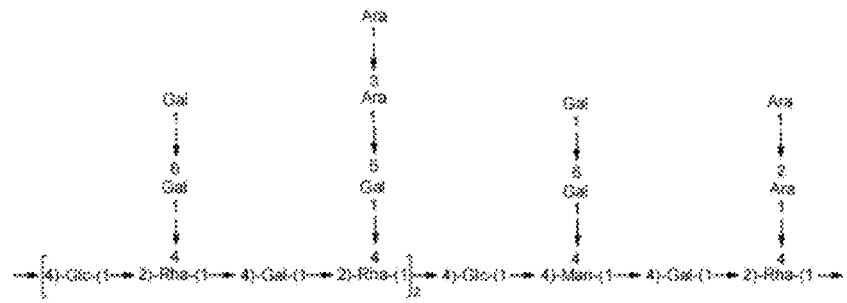
FIGS. 6A-6D: proposed structures of polysaccharides present in the extract. The degree of substitution and the length of side chains may vary among the individual fractions. Ara=arabinose; Gal=galactose; GalUA=galacturonic acid; Glc=glucose; GlcUA=glucuronic acid; Man=mannose; Rha=rhamnose.
Figure 6B:
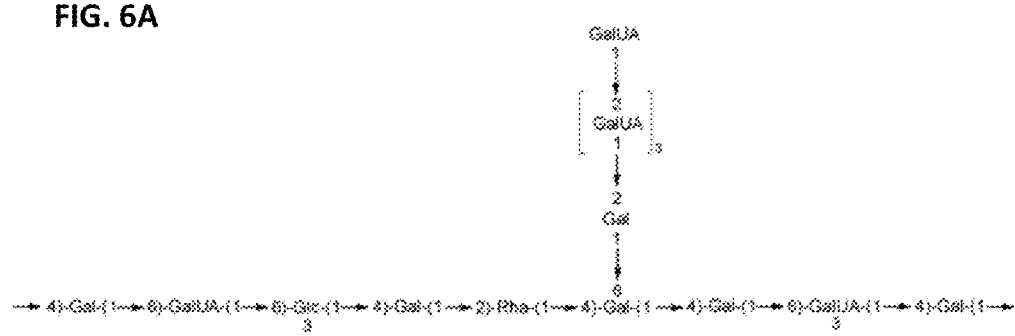
Figure 6C:
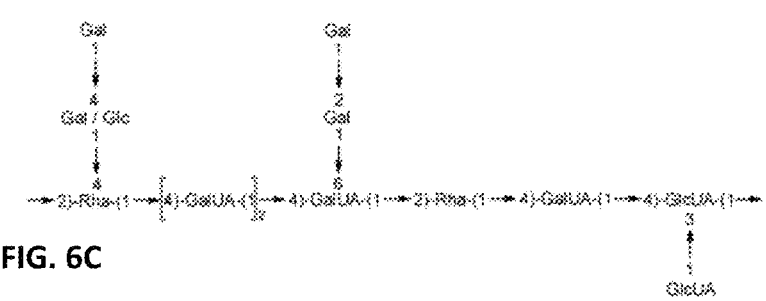
Figure 6D:
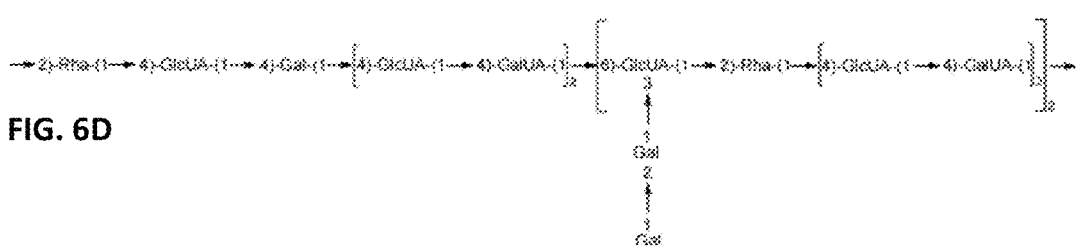

Determination of Progressive Motility of Recovered Human Spermatozoa in Mucilaginous Extract Approximately 10 µL of separated motile spermatozoa in mucilaginous extract was withdrawn from each capillary tube diluted in 190 µL of human tubal fluid (HTF) medium containing 0.5% human serum albumin (HSA) and 20 mM HEPES (HTF-HEPES; pH, 7.4), and a drop of the resulting solution was placed on a microscope slide. The percentage sperm motility was quantified manually with a phase contrast microscope. Spermatozoa were considered to be progressively motile if they moved in a linear manner from one point to another. The percentage of progressively motile spermatozoa was determined twice for each sample by a certified clinical andrologist on 100 cells in different fields, with a laboratory counter and averaged. Counts were accepted as accurate if each of the two counts did not differ by 10%. The grade of motion on a scale of 0 to 4 was determined subjectively. The grade and percentage progressive motility of mucilaginous extract-penetrated spermatozoa were 3.5-4.0 and 86.8%, respectively, compared with those of the control (2.5-3.0, 47.7%, respectively). The above procedure was carried out using the sperm from patients (N=5) undergoing fertility evaluation to determine whether their spermatozoa would penetrate the mucilaginous extract. FIG. 5 shows that the spermatozoa from an infertile patient that did not penetrate the mucilaginous extract. These data suggest that mucilaginous extract can substitute for CF for testing sperm function.

Figure 3A:
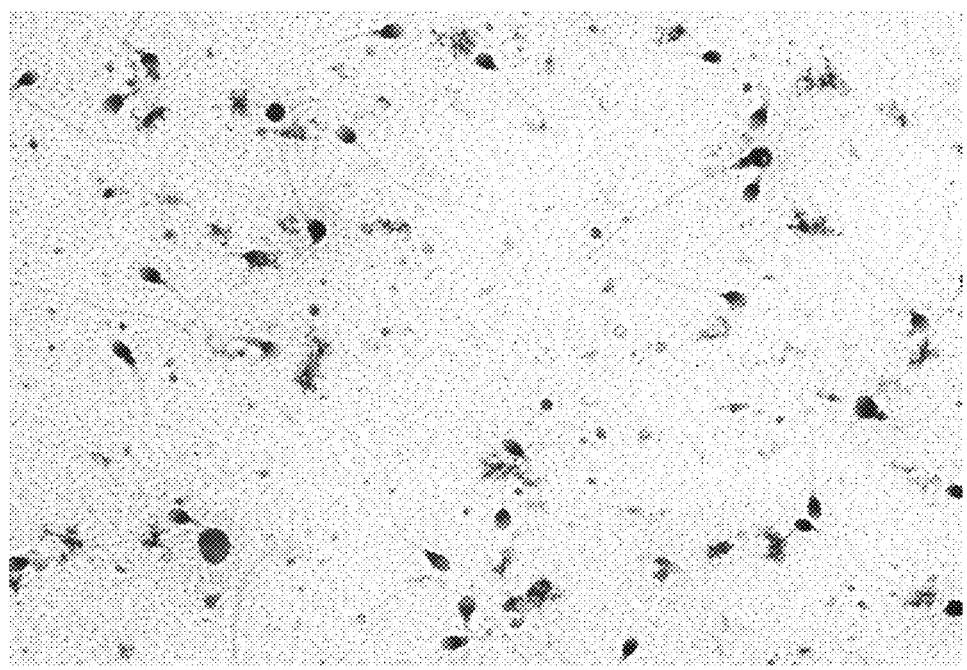
FIGS. 3A-3B: comparison of the morphology of spermatozoa in the semen control (FIG. 3A) and in the mucilaginous extract (FIG. 3B).
Figure 3B:
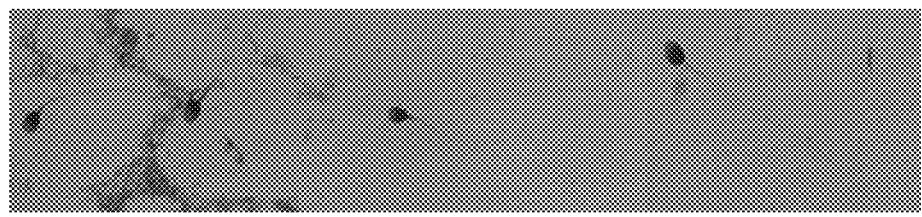
Figure 4:
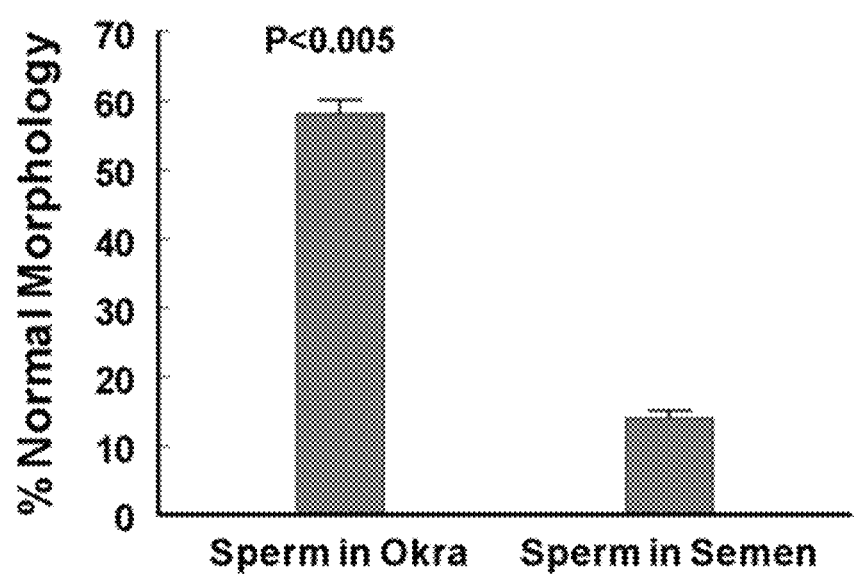
FIG. 4: Percentage of normal morphological spermatozoa in mucilaginous extract vs. semen control.

Determination of Morphology of Recovered Human Spermatozoa in Mucilaginous Extract Sperm morphology assessment of spermatozoa in mucilaginous extract was conducted by a certified clinical andrologist. Feathered smears of approximately 10 µL each of undiluted mucilaginous extract containing human spermatozoa and matching semen (control; N=5/group) were prepared on ethanol-cleaned glass slides and left to dry in a dust free chamber. Subsequently, smears were fixed and stained with reagents in a modified Papanicolaou staining kit (Spermac, Stain Enterprises, South Africa) according to the manufacturer's instructions and sperm morphologies assessed using the Kruger strict criteria with a phase contrast microscope equipped with a scaler. A spermatozoon was considered normal if the head had a smooth, oval shape with a well-defined acrosome comprising approximately 40-70% of the head area. Morphologically, the sperm head must be 5.0-6.0 µM long and 2.5-3.5 µM wide to be considered normal. In addition, a spermatozoon was considered normal if it was devoid of neck, midpiece, or tail defects and no cytoplasmic droplet of more than half the size of the head. All borderline morphologic forms of spermatozoa were considered abnormal. The slides are shown in FIG. 3. The mean percentage of normal morphological form of spermatozoa in the mucilaginous extract samples is much greater than in the semen sample (control; see FIG. 4).

J. Example 3: Sperm Longevity and Viability after Thawing

Methods

Okra Mucus Extraction:

Fresh okra was purchased from local grocery stores and mucus was extracted as described above.

Semen and Processing:

Discarded de-identified semen samples that met criteria of WHO for normal semen samples (1.5-5.0 mL volume, 7.2-8.2 pH, 40% or greater motility, concentration=20×10 million/mL) were used in the freezing protocol with okra mucus. Each semen sample was divided into halves to be frozen in conventional freezing medium consisting of TEST Yolk Buffer containing 12% glycerol (volume/volume) and 10 μg gentamicin/ml (Irvine Scientific, Santa Ana, Calif.) or in the presence of okra mucus. Each half of semen samples designated for freezing in the presence of okra mucus was diluted with equivalent volume of human tubal fluid (HTF) buffer containing 25 mM sodium bicarbonate (HTF-buffer) and 25% okra mucus (volume/volume) from a 30% okra extract. The remaining half was similarly diluted with HTF medium only. Subsequently, an equivalent volume of TEST-Yolk buffer to each diluted semen sample was added dropwise with gentle mixing to a homogenous suspension with a final glycerol concentration of 6.0% (volume/volume), final okra dilution in ready to freeze preparation=12.5% (volume/volume of the 30% extract) and placed on ice for approximately 15 hours. Prior to subjecting each sample to freezing conditions, 10 μL of cooled TEST-Yolk-extended semen sample was withdrawn and placed on a clean glass slide, covered with cover glass and allowed to warm to room temperature (37° C.) before post cooling evaluation of percentage sperm motility was conducted with a phase contrast microscope and a laboratory counter. Cooled TEST-Yolk-extended semen samples were then subjected to liquid nitrogen (LN) vapor phase freezing for 30 minutes and subsequently stored immersed in LN. Samples were allowed to remain in LN storage for at least 24 hour before thawing. Samples were thawed to room temperature and subsequently diluted with two volumes of warm (37° C.) HTF-buffer in order to elute the cell penetrating cryoprotectant (glycerol) from the cytoplasm of the cryopreserved spermatozoa. Frozen-thawed human spermatozoa were subjected to phase contrast microscopy to determine the motility status of each sample as described above.

Acrosomal Status of Post-Thaw Motile Spermatozoa and Longevity:

After the assessment of post-thaw sperm motility, control and okra mucus-exposed samples subjected to gradient (ISOLATE, Irvine Scientific; 80%) centrifugation to separate motile from non-motile spermatozoa. Subsequently, motile spermatozoa were permeabilized in cold (−20° C.) 90% ethanol and stained with FITC-conjugated lectin (Vector Labs, Burlingame, Calif.). Following FITC-lectin staining, spermatozoa were subjected to epi-fluorescence microscopy. Spermatozoa with green even fluorescence in the acrosomal region were considered acrosome intact and therefore to lack damage to the membrane. Spermatozoa with fluorescence in the equatorial region of the cell were considered acrosome reacted and therefore to have sustained membrane damage.

Longevity of Non-Frozen Human Spermatozoa in Okra Mucus:

Liquefied freshly ejaculated human semen samples were washed with HTF containing 20 mM HEPES and 0.5% BSA (HTF-HEPES; pH 7.4) following which each sperm suspension was subjected to a continuous gradient wash as described above for the purpose of harvesting highly motile cells. Each sample of highly motile cells was divided into two to be cultured in HTF-buffer or HTF-buffer+25% okra mucus (volume [30% okra mucus in HTF-buffer]/volume [HTF-buffer]) for 18 hours in an atmosphere of 5% $CO_2$ in air in a humidified incubator.

Results

Figure 7:
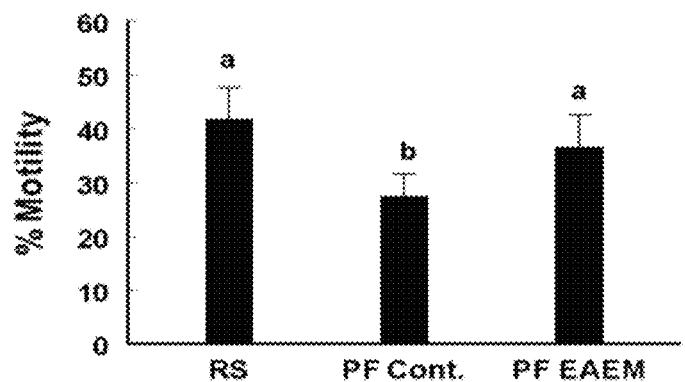
FIG. 7: Sperm motility during slow cooling in okra mucus.
Figure 8:
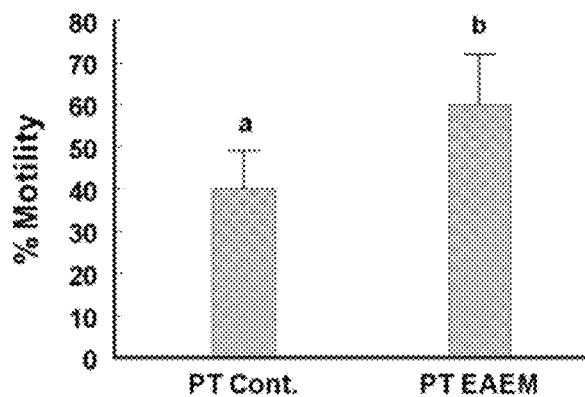
FIG. 8: Post-thaw sperm motility in okra mucus.
Figure 9:
FIG. 9: Acrosomal status/membrane integrity of frozen-thawed human spermatozoa.

During the pre-freezing period (PF), cooled spermatozoa in the base freezing buffer (control; PF control; FB) sustained a significant reduction in mean percentage motility (p<0.02) compared with those in cooled base freezing buffer supplemented with okra mucus (PF OK) or those in raw semen (RS). Further, supplementation of base freezing buffer with okra mucilage maintained a similar percentage motility rate observed in RS. (Graphs with different superscripts are statistically different; FIG. 7; graphs with different superscripts are statistically different). Freezing human semen in extracted *Abelmoschus esculentus* mucilage (EAEM) increased the percentage of post-thaw motile sperm population compared with FB (P<0.03; FIG. 8; graphs with different superscripts are statistically different). FIG. 9 shows a micrographic image of the frozen-thawed spermatozoa.

This observation suggests that more post-thaw motile spermatozoa can be harvested after freezing in EAEM for increased efficacy of affordable assisted reproductive technologies (ART) such as intra uterine insemination (IUI). Interestingly, spermatozoa in semen samples frozen in EAEM had a higher (P<0.05) percentage motility (35.3+ 3.4%) compared with those frozen in FB (23.5+4.1%), 8 hr post-thaw.

Regardless of the freezing medium, the highly motile spermatozoa harvested via gradient centrifugation maintained their membrane integrity. This suggests that if more motile spermatozoa are harvested based on higher percentage motility observed among cells frozen in EAEM, freezing in EAEM can facilitate the collection of a significant number of motile spermatozoa.

Figure 10:
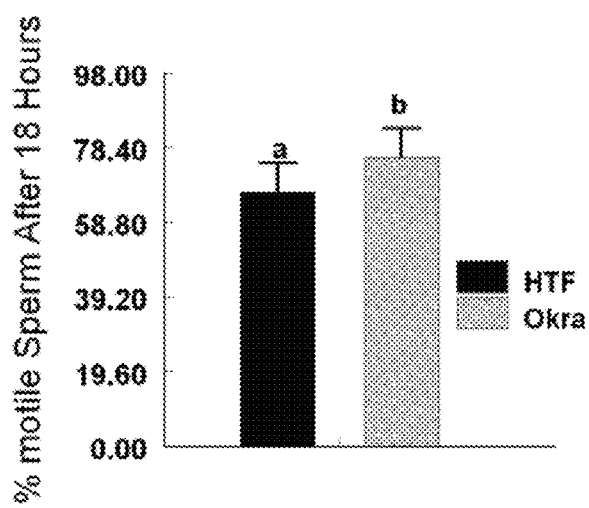
FIG. 10: Enhanced longevity of human spermatozoa in HTF supplemented with okra mucus.

Highly motile spermatozoa (92.4±8%) harvested via continuous gradient centrifugation that were cultured for 18 hours in HTF-buffer supplemented with okra mucus had a higher percentage of motile spermatozoa (P<0.05; FIG. 10) than their counterparts cultured in HTF-buffer-only (graphs with different superscripts are statistically different). The result of this experiment indicates that culturing spermatozoa in the presence of okra mucus protects more spermatozoa to remain motile during a protracted period. The ability of okra mucus to maintain longevity in more cells than their counterparts cultured in HTF-only indicates that it has the potential to maintain more cell in motile state in women with a compromised cervix.

K. Example 4: Human Sperm/Okra Mucus Penetration Test

A test was conducted to determine whether okra mucilage functions as an effective medium to measure sperm penetration. Microscope slides were cleaned with 70% ethanol and thoroughly wiped dry with a task wipe. Subsequently, double-sided tape was applied to the clean glass slide, leaving a longitudinal strip uncovered approximately 50×2 mm (the "sperm lawn"). This was followed by the application of cover glass and pressed gently to eliminate air bubbles and firmly secure the cover glass. Thereafter, okra mucus extracted as described above was applied steadily to the 10° angled uncovered side of the glass slide to permit the mucus to penetrate the sperm lawn without air bubbles. The mucus loaded slide was placed in a 100×20 mm FALCON style polystyrene nonpyrogenic Petri dish (Corning, Inc., Corning, N.Y.) and placed in a humidified incubator with an atmosphere of 37° C. and 5.0% $CO_2$ for about 45 minutes for the mucus to attain zero movement (acquire static status). Subsequently, 10 μL of semen was carefully placed in the okra mucus, just before the edge of the cover glass and incubated as described above for 30 minutes. Post incubation, the preparation was subjected to phase contrast microscopy at a magnification of 200× for sperm penetration of the mucus, phalange (finger-like projections of the seminal fluid into the okra mucus creating an interface between the two substances) formation and distance traveled down the sperm lawn from the loading zone.

All preparations developed phalanges. However, spermatozoa in semen samples (N=5) that did not meet the WHO criteria for normalcy had zero to poor transition and traveling distance (mean=1.75±0.8 cm) with the number of motile spermatozoa in first microscopic field (F1) from the tip of a phalange showing 7 cells, F2 showing 10 cells, and F3 showing 9 cells. Spermatozoa in semen that met the WHO criteria for normalcy were superior (P<0.05) in their transition and travel distance in the sperm lawn. The mean distance traveled by spermatozoa in normal samples (N=7) was 4.23±0.05 cm in 30 minutes. The F1, F2, and F3 for spermatozoa in normal semen samples were 48 cells, 45 cells, and 39 cells, respectively.

Implications:

The observations made in this study indicate that the preparation described above has the potential to be utilized as a replacement cervical mucus kit. Okra mucus-loaded slides as described above can be prepared and snap frozen and used when needed by thawing in a humidified chamber as described above followed by semen application, incubation as described above and evaluated for phalange formations, transition of spermatozoa into okra mucus, evaluation of the number of motile spermatozoa in microscopic fields from the phalanges and distance traveled.

L. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed:

1. A substantially clear mucilaginous extract of the fruit of *Abelmoschus esculentus* that is the product of the process of (a) extracting a fruit of *A. esculentus* in human tubal fluid, to produce a first extract; (b) separating a substantially clear mucilaginous fluid from the first extract to form the substantially clear mucilaginous extract, wherein the substantially clear mucilaginous extract comprises human tubal fluid and has at least one of the following properties: lacks visible green coloration; a Spinnbarkeit of at least about 10 cm when measured according to a Spinnbarkeit test; displays ferning when subjected to a fern test; and when a semen sample is subjected to a sperm-mucus penetration test using the substantially clear mucilaginous extract in place of cervical mucus, spermatozoa that penetrate into the substantially clear mucilaginous extract have a significantly better indication of fertility than do sperm in the semen sample.

2. The substantially clear mucilaginous extract of claim 1, wherein the substantially clear mucilaginous extract has all of the following properties: a Spinnbarkeit of at least about 10 cm when measured according to a Spinnbarkeit test; displays ferning when subjected to a fern test; lacks visible green coloration; and when a semen sample is subjected to a sperm-mucus penetration test using the substantially clear mucilaginous extract in place of cervical mucus, spermatozoa that penetrate into the substantially clear mucilaginous extract have a significantly better indication of fertility than do sperm in the semen sample.

3. The substantially clear mucilaginous extract of claim 1, wherein the extracting comprises boiling the fruit of *A. esculentus* in the human tubal fluid.

4. The substantially clear mucilaginous extract of claim 1, wherein the extracting comprises contacting the fruit of *A. esculentus* with the human tubal fluid at a temperature of about 4° C. for about 4 hours.

5. The substantially clear mucilaginous extract of claim 1, wherein the human tubal fluid comprises at least one of bicarbonate-buffered human tubal fluid and human serum albumin.

6. The substantially clear mucilaginous extract of claim 5, wherein the substantially clear mucilaginous extract comprises at least one of bicarbonate-buffered human tubal fluid and human serum albumin.

7. The substantially clear mucilaginous extract of claim 5, wherein the substantially clear mucilaginous extract comprises 0.5% w/v of at least one of bicarbonate- buffered human tubal fluid and human serum albumin.

8. The substantially clear mucilaginous extract of claim 1, wherein the substantially clear mucilaginous extract comprises a plurality of polysaccharides, and wherein the extract is at least 10% mol/mol galactose, uronic acids, and protein upon hydrolysis of the polysaccharides.

9. The substantially clear mucilaginous extract claim 1, wherein the substantially clear mucilaginous extract comprises a plurality of polysaccharides, and wherein the extract comprises 7-28% mol/mol rhamnose, 12-50% mol/mol galactose, 14-56% mol/mol uronic acids, and 12-48% mol/mol protein upon hydrolysis of the polysaccharides.

10. The substantially clear mucilaginous extract of claim 1, wherein the substantially clear mucilaginous extract comprises polysaccharides shown in A-D below:

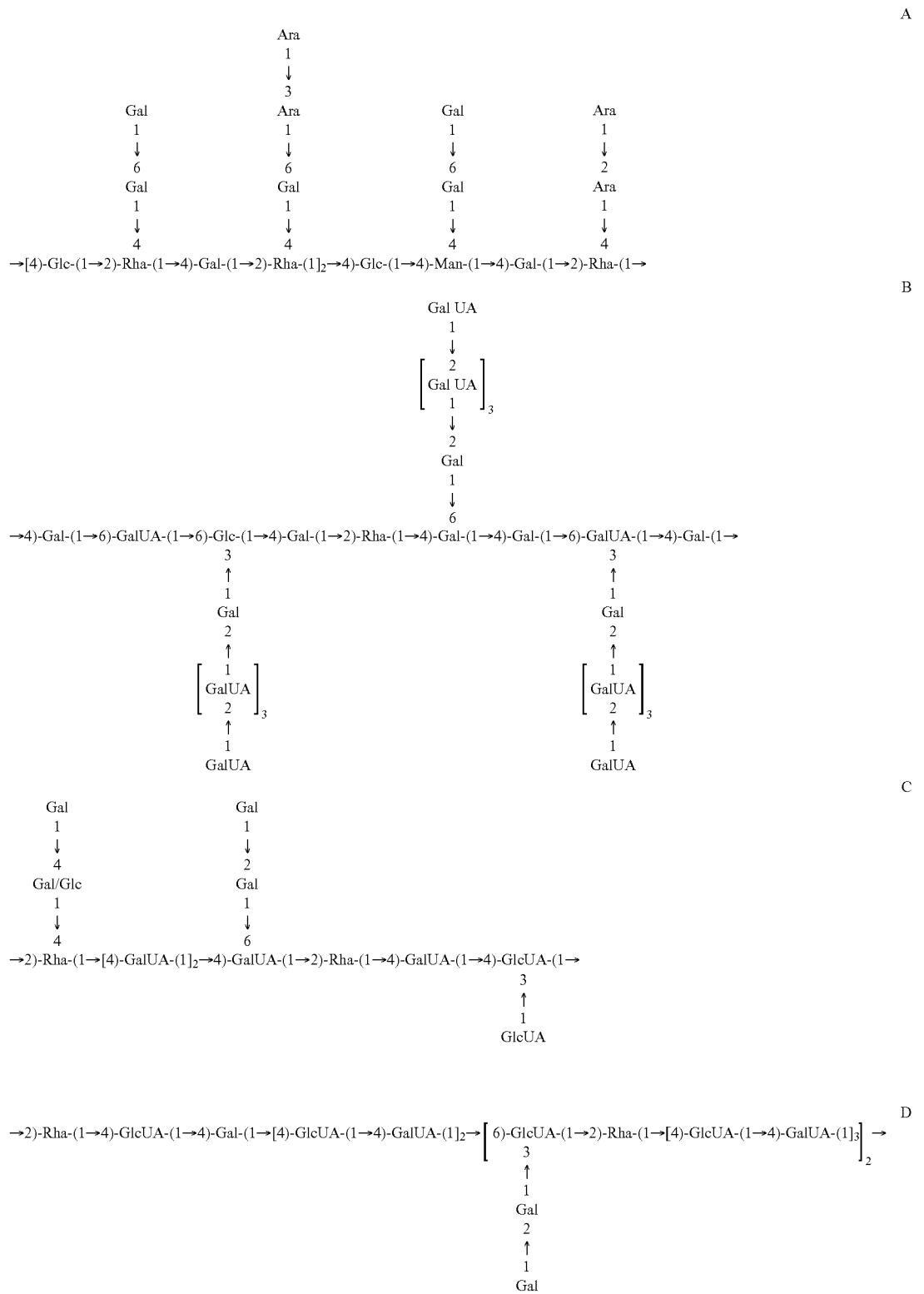

11. The substantially clear mucilaginous extract of claim 1, wherein extracting a fruit of *A. esculentus* in human tubal fluid, to produce a first extract, comprises extracting a fruit of *A. esculentus* in human tubal fluid containing at least one of human serum albumin or bovine serum albumin.

12. The substantially clear mucilaginous extract of claim 1, wherein the substantially clear mucilaginous extract is free of chlorophyll pigment.

13. A storage medium for spermatozoa, the medium comprising a multiplicity of spermatozoa and an effective amount of the substantially clear mucilaginous extract of the fruit of *Abelmoschus esculentus* of claim 1.

14. The storage medium of claim 13, comprising a cryopreservative agent at a concentration effective to maintain greater than 40% sperm motility after freezing for 24 h.

15. The storage medium of claim 13, comprising an antimicrobial agent.

16. The storage medium of claim 13, further comprising at least one of: semen; bicarbonate buffered HTF medium; glycerol at a cryopreservation-effective concentration; egg yolk; and gentamicin at a concertation effective to reduce the likelihood of microbial contamination.

17. The storage medium of claim 13, wherein said storage medium is a cryopreservation medium.

18. The storage medium of claim 13, wherein the mucilaginous extract lacks visible green coloration.

19. The storage medium of claim 13, wherein the significantly better indication of fertility comprises a significantly higher rate of at least one of normal morphology, progressive motility, or significantly higher grade of motility.

20. The storage medium of claim 13, the process comprising straining the first extract through one or more pores having an effective pore size of about 1 mm or less.

21. The storage medium of claim 13, wherein the aqueous medium comprises at least one of:
  bicarbonate-buffered human tubal fluid, and
  at least one of bovine serum albumin and human serum albumin.

22. A method of artificial insemination, the method comprising inseminating a subject with a suspension of spermatozoa, the suspension comprising a multiplicity of spermatozoa suspended therein and an effective amount of the substantially clear mucilaginous extract of the fruit of *Abelmoschus esculentus* of claim 1.

* * * * *